(12) United States Patent
Greenstein

(10) Patent No.: US 6,510,332 B1
(45) Date of Patent: Jan. 21, 2003

(54) ELECTRODE LEADS FOR USE IN LAPAROSCOPIC SURGERY

(75) Inventor: Robert J. Greenstein, Tenafly, NJ (US)

(73) Assignee: Transneuronix, Inc., Mt. Arlington, NJ (US)

( * ) Notice: Subject to any disclaimer, the term of this patent is extended or adjusted under 35 U.S.C. 154(b) by 0 days.

(21) Appl. No.: 09/640,201

(22) Filed: Aug. 16, 2000

Related U.S. Application Data

(60) Provisional application No. 60/151,459, filed on Aug. 30, 1999.

(51) Int. Cl.[7] ............................. A61B 5/042; A61N 1/05
(52) U.S. Cl. ...................... 600/377; 607/116; 607/133
(58) Field of Search ................................. 600/374, 375, 600/377, 373; 607/116, 129, 130, 132, 133

(56) References Cited

U.S. PATENT DOCUMENTS

| | | |
|---|---|---|
| 2,865,376 A | 12/1958 | Pellier et al. |
| 3,760,812 A | 9/1973 | Timm et al. |
| 4,444,207 A | 4/1984 | Robicsek |
| 4,475,560 A | 10/1984 | Tarjan et al. |
| 4,524,771 A | 6/1985 | McGregor et al. |
| 4,901,722 A | 2/1990 | Noguchi |
| 5,059,207 A | 10/1991 | Shah |
| 5,100,431 A | 3/1992 | Buster et al. |
| 5,217,471 A | 6/1993 | Burkhart |
| 5,242,458 A | 9/1993 | Bendel et al. |
| 5,292,344 A | 3/1994 | Douglas |
| 5,308,318 A * | 5/1994 | Plassche, Jr. ................ 604/540 |
| 5,423,872 A | 6/1995 | Cigaina |
| 5,423,876 A | 6/1995 | Camps et al. |
| 5,433,728 A | 7/1995 | Kim |
| 5,450,739 A | 9/1995 | Bogart et al. |
| 5,489,294 A | 2/1996 | McVenes et al. |
| 5,613,973 A * | 3/1997 | Jackson et al. ................ 606/1 |
| 5,690,691 A | 11/1997 | Chen et al. |
| 5,716,392 A | 2/1998 | Bourgeois et al. |
| 5,836,994 A | 11/1998 | Bourgeois |
| 5,861,014 A | 1/1999 | Familoni |
| 5,897,586 A * | 4/1999 | Molina ........................ 600/374 |
| 5,995,872 A | 11/1999 | Bourgeois |
| 6,041,258 A * | 3/2000 | Cigaina et al. ................ 607/40 |
| 6,146,391 A | 11/2000 | Cigaina |

FOREIGN PATENT DOCUMENTS

| | | |
|---|---|---|
| DE | 44 02 058 | 1/1994 |
| WO | WO 97 41921 | 11/1997 |

\* cited by examiner

*Primary Examiner*—Lee Cohen
(74) *Attorney, Agent, or Firm*—Fitch, Even, Tabin & Flannery

(57) ABSTRACT

This invention relates to an implant device which is designed and adapted use in laparoscopic surgery. This implant device is especially adapted for electrostimulation and/or electrical monitoring of endo-abdominal tissue or viscera. The implant device has an elongated body having on, or near, its distal end a flexible attachment member which can be folded back on to the elongated body and attached to the elongated body thereby forming a closed loop around the tissue of interest. By "looping" around or through the tissue of interest, the attachment member and the elongated body are securely attached to the tissue and will resisted displacement even in cases where the tissue is subject to vigorous, periodic peristaltic movement within the body (e.g., digestive organs). One preferred implant device of this invention has an elongated body equipped with two or more electric poles that are electrically connected to an electric connection terminal for connection to a power source, mechanism to penetrate the tissue or viscera to be treated, quick-release connecting devices to separate the penetration device from the elongated body, and a locking or attachment device which is capable of folding back and attaching to the elongated body whereby the locking device and the elongated body forms a secure and essentially continuous loop around the tissue or viscera to be treated.

28 Claims, 4 Drawing Sheets

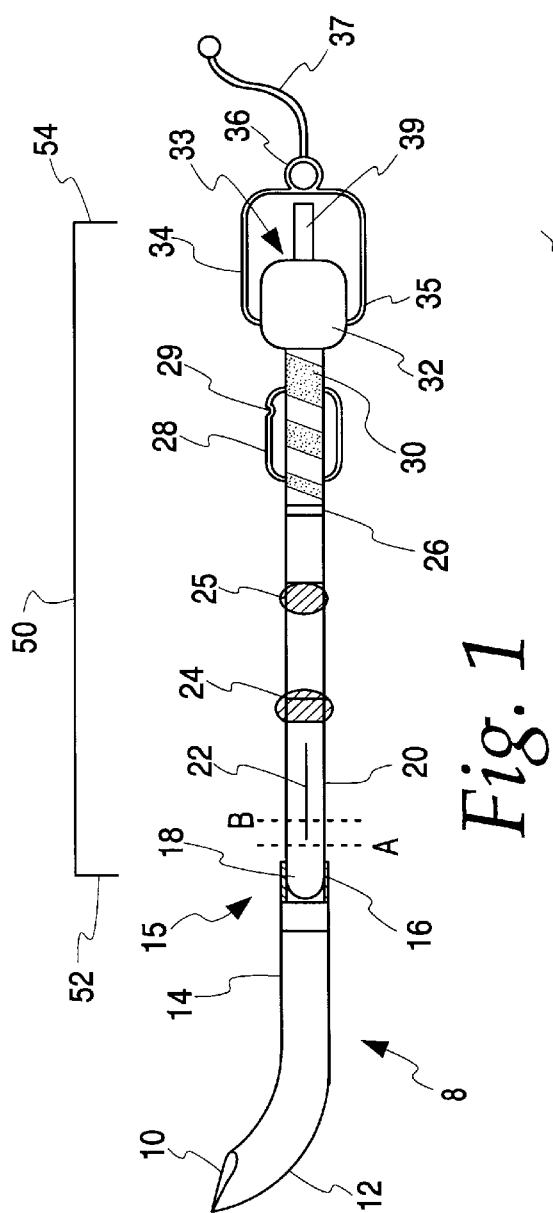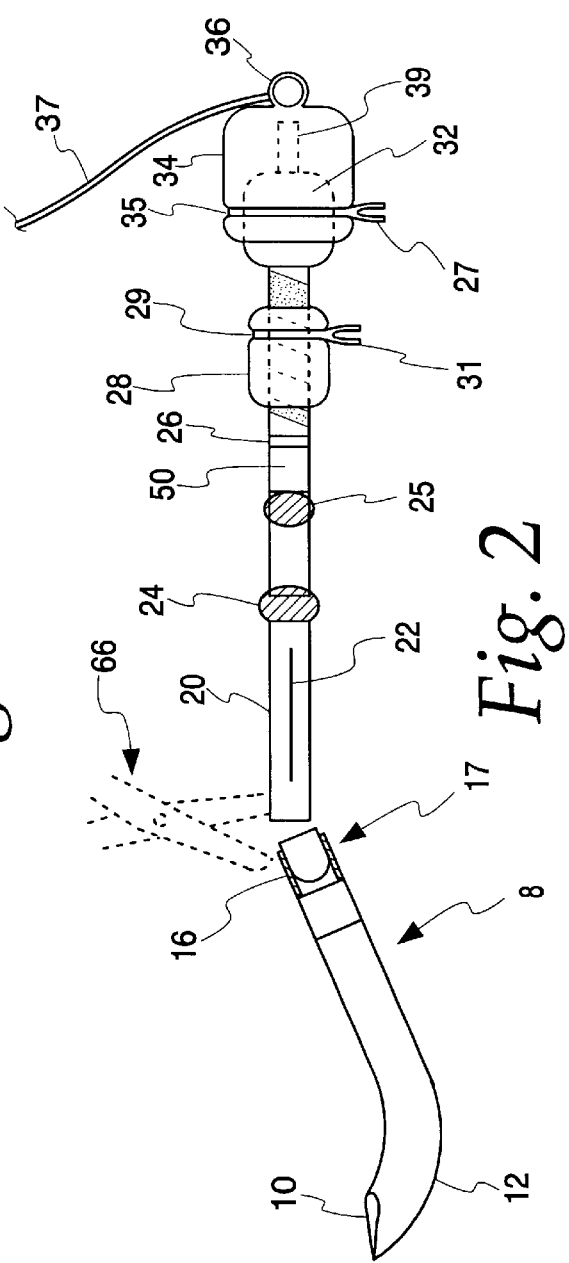

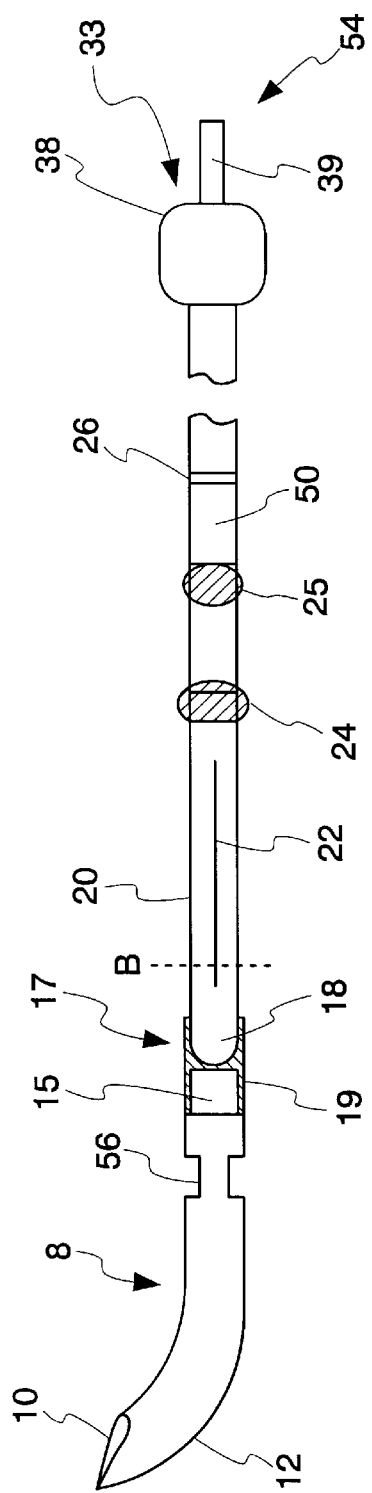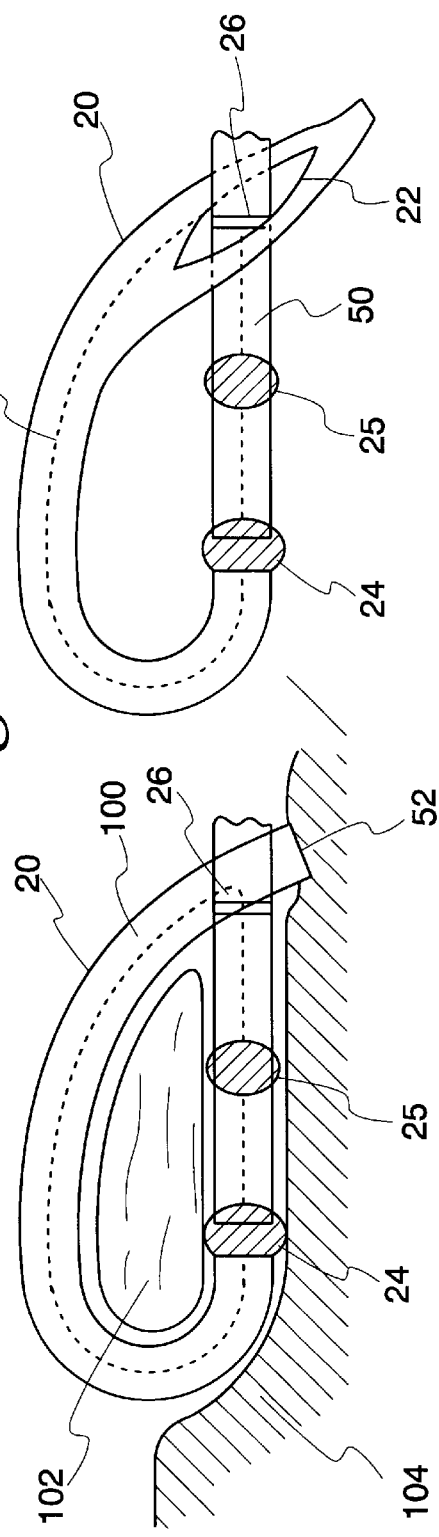

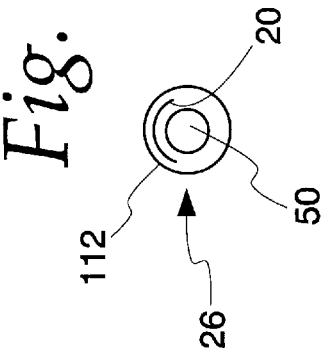
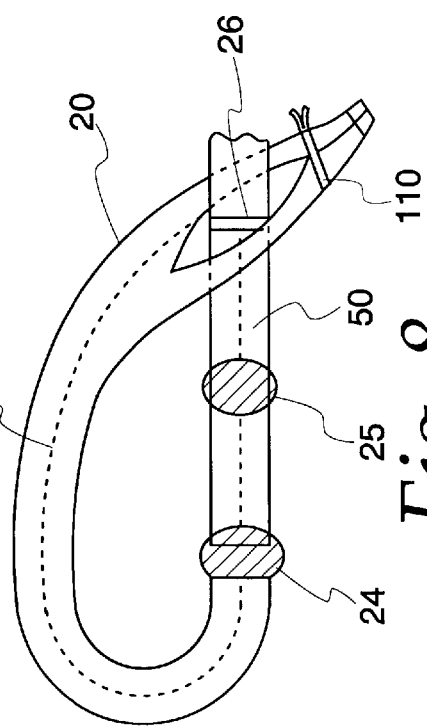
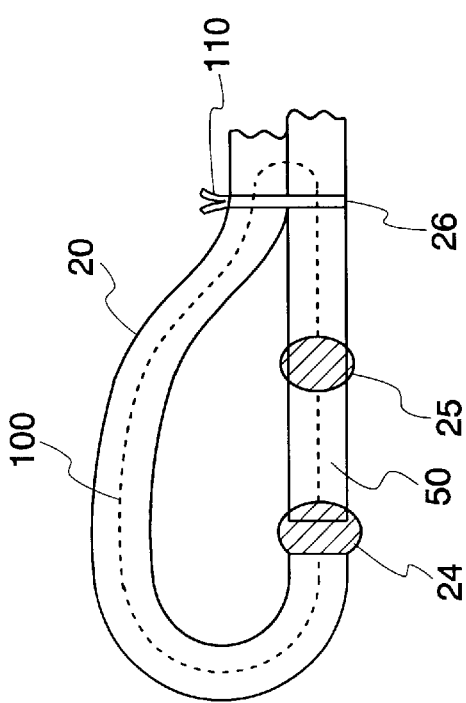
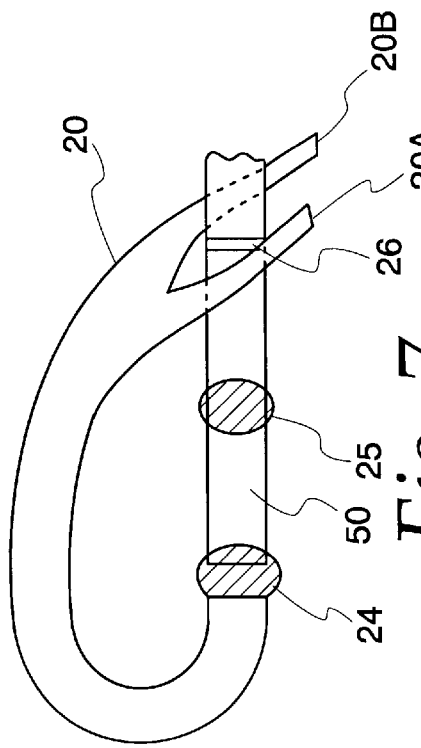

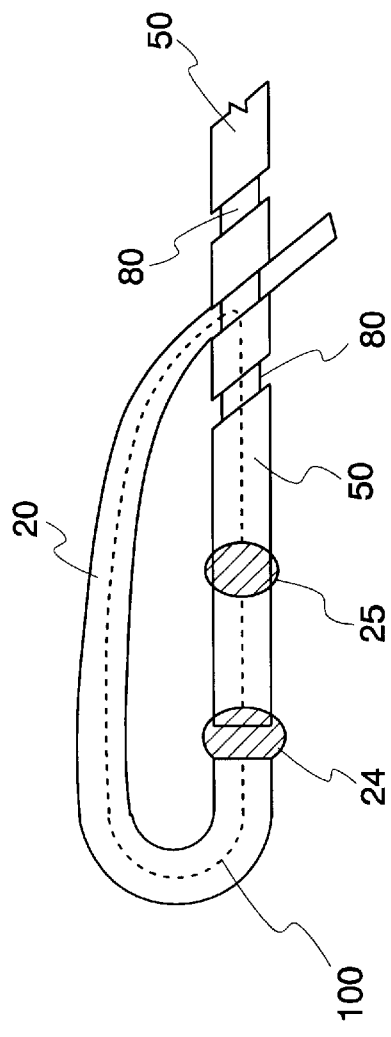
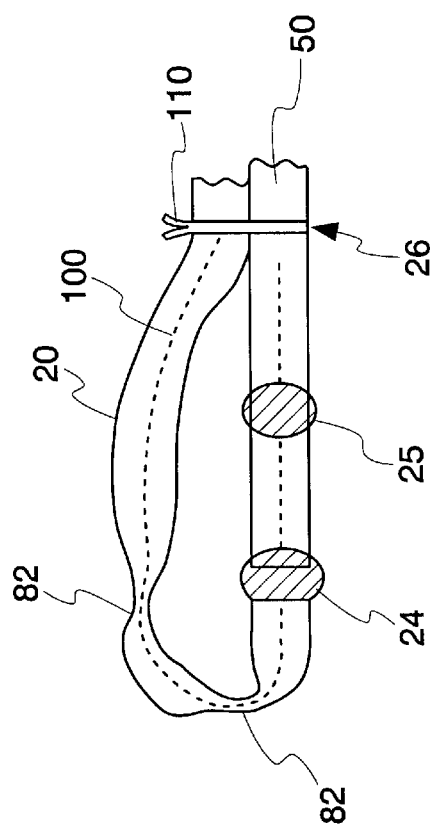
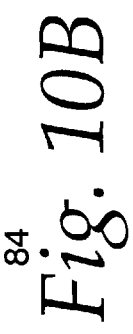

ELECTRODE LEADS FOR USE IN LAPAROSCOPIC SURGERY

This application claims the benefit of Provisional application Ser. No. 60/151,459, filed Aug. 30, 1999.

FIELD OF THE INVENTION

This invention relates to a medical implant device for electrostimulation and/or electrical monitoring of endo-abdominal tissue or viscera. More specifically, this invention provides a medical implant device having electrode leads which can be attached or affixed to the enteric or endo-abdominal tissue or viscera such that the electrode leads resist detachment in spite of the vigorous and/or periodic action or movement of the enteric or endo-abdominal tissue or viscera. The medical implant device of this invention is especially adapted for location or implantation in the endo-abdominal cavity over extended periods of time.

BACKGROUND OF THE INVENTION

It is well known that more than 70% of illnesses affecting the digestive tract are of a functional nature. Today such illnesses are treated predominantly using pharmacological means. Since drugs generally have side effects, particularly when the drugs cure the symptom and not the underlying problem or dysfunction, they must often be administered temporally. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exits of correcting dysfunction by means of electrostimulation applied at specific frequencies, sites, and modalities and with regard to the self-regulating electromotor physiology of the gastrointestinal organs or tract. It has recently been shown, for example, that changes occur in the motility and electromotor conduct of the gastric tract in eating disorders (e.g., obesity, thinness, bulimia, anorexia). Disturbances in electromotor activity in diabetic gastroparesis, reflux in the upper digestive tract, and numerous other gastroenterological functional pathologies have also been observed.

Stimulation of the intrinsic nervous system of the stomach is likely to have two major consequences or effects: (1) the correction and direct control of the electromotor activity of the intestines and (2) the stimulation of increased incretion of specific substances (i.e., gastroenteric neuromediators) produced by the intrinsic nervous system itself through the myenteric plexus. Curing of functional illnesses involving the digestive system and, more broadly, involving disorders in any way connected to, or associated with, the digestive system is, therefore, closely linked to the progress of research in the field of electrophysiology.

An indispensable condition for modifying the electrical activity of the digestive system's intestinal tract and related neurohormonal incretions is the use of an implant system to generate electrical impulses (electrical stimuli) and means (e.g., electrocatheters) to connect them to the viscera and/or intestines to be stimulated. These treatment methods involve an "invasive" surgical technique to implant the electrocatheter in the abdomen. This may involve open or, preferably, micro-invasive surgery (i.e., video-laparoscopic surgery). Current electrocatheters to stimulate electrically and/or monitor endo-abdominal viscera normally have metal microbarbs which are angled in such a way as to permit application of the end of the catheter and to prevent it subsequently from being dislodged. However, this type of catheter is often very complicated to make and, consequently, is very costly. Moreover, metal microbarbs can damage surrounding tissue especially when exposed to the vigorous action of the digestive tissue and/or organs. Among the undesirable consequences of such damage is evasion of the electrode into the lumen of the gastrointestinal tract. This would result in contamination of the abdominal cavity and the electrode. The subsequent infection would, at a minimum, require removal of the catheter and involve an additional operation.

During laparoscopic procedures, after administering a general anesthetic, the patient's abdomen is inflated with $CO_2$ or another inert inflammable gas, thereby transforming the abdominal cavity from a virtual to a real cavity. Rigid tubes with air-tight valve mechanisms ("trocars") are then inserted into the gas-filled abdominal cavity so that a video camera and other surgical instruments can be introduced into the abdomen. The operation then proceeds by viewing the video images transmitted by the camera. Multiple trocars are required. Generally, the first trocar provides access to the abdomen by the video camera in order to monitor the surgical procedure. A clamp is normally inserted in the second trocar to move or retain the hepatic edge that normally covers the lesser curve of the stomach or other viscera depending on the type of operation to be performed. A third trocar provides access for a maneuvering clamp or laparoscopic forceps. The fourth trocar is used for the introduction of instruments as well as the electrocatheter to be implanted in the stomach wall of the patient. The structure of the electrocatheter plays an important part in facilitating the specific operation for whichever of the patient's organs and/or viscera the surgeon aims to stimulate.

Each of the trocars used, of course, requires a separate tract through the skin and abdominal wall. To keep the abdomen inflated, valves are used with the trocars to provide a gas-tight seal. Introduction of a medical device, such as an electrocatheter or implantable electrode, into the abdomen generally requires the use of laparoscopic forceps to grasp the device. Such devices, which are generally inherently fragile in nature, could be damaged if grasped too firmly by the forceps. Thus, for example in the case of an electrocatheter having electrode leads, the interior conductor wires could be broken, rendering the device dysfunctionally or completely useless.

It is, of course, desirable in laparoscopic surgery to limit the number of trocars used since each trocar requires a separate incision which results in additional visible scars for the patent. More importantly, each additional incision increases the chance of infection and other complications resulting therefrom. Therefore, to reduce the number of trocars required, implantable devices are often inserted completely through the trocar and into the abdomen so that a single trocar can serve for multiple uses (e.g., for insertion of other instruments and/or manipulation devices). Thus, the surgeon will often need to pull the distal end of the inserted device back through a trocar and/or remove the device entirely. In this case, the device needs to "line up" to the trocar passageway to be pulled back through the trocar. Of course, if the device is grasped by the forceps in a manner so the longitudinal dimension of the device is not alined with the trocar passageway, the device cannot be pulled back through the trocar.

It is also desirable to place the electrocatheter adjacent to the tissue or organ of interest and "lock" it in place so that the target tissue or organ can then be electrostimulated and/or electrically monitored. As noted above, metal microbarbs have been used to lock the device in place. Such metal microbarbs can damage or tear surrounding tissue—especially when the implant device is subjected to the vigorous action or peristaltic movement of the digestive organs. More recently, flexible microbarbs have been used for such implant device. Although such flexible microbarbs are less likely to damage the surrounding tissue, so-equipped electrocatheters are prone to displacement when acted on by the vigorous action or movement of the digestive organs, especially when the implant device is to remain within the patient for prolonged periods of time. Additionally, the peristaltic movement may fracture the barbs, or cause erosion through the organ wall and into the lumen of the organ to which it was affixed. Once displaced, of course, the implant device can no longer provide the desired electrostimulation and/or electrical monitoring of the target tissue. Moreover, the displaced implant device may, over time, move within the body cavity to locations remote from the initial location thereby causing complications and making surgical removal more difficult. Moreover, such movement will, of course, render the implant device inoperative with regard to the initially targeted tissue and may require an additional medical procedure to retrieve and/or reposition the implant device proximal to the target tissue.

It would be desirable, therefore, to provide an improved implant device which can be easily positioned and attached or tethered to the target tissue or organ and which can then be securely locked in place. It would also be desirable to provide an improved implant device with a locking or attachment mechanism which is less likely to damage surrounding tissue, especially where the tissue is undergoing repeated and/or vigorous movement. It would also be desirable to provide an improved implant device which will resist displacement by the vigorous movement of internal organs or viscera within the abdominal or other body cavities over prolonged or extended periods of time. The present invention provides such implant devices. Although the implant devices of the present invention are especially adapted for implantation within the abdominal cavity, they can also be used throughout the body. The present implant devices can effectively "lock-on" and resist displacement from tissue or organs which undergo repeated and/or vigorous movement. The present implant device would be especially useful, for example, within the abdominal cavity or the thoracic cavity.

SUMMARY OF THE INVENTION

This invention relates to an implant device which is designed and adapted for use in laparoscopic surgery. This implant device is especially adapted for electrostimulation and/or electrical monitoring of endo-abdominal organs, tissue, or viscera. The implant device of this invention has an elongated body having on, or near, its distal end a flexible attachment mechanism or member which can be folded back onto the elongated body and attached to the elongated body, thereby forming an essentially closed loop around or through the tissue of interest. By "looping" around or through the tissue of interest, the attachment member and the elongated body are securely attached to the tissue and can resist displacement even in cases where the tissue is subject to vigorous peristaltic movement within the body (e.g., movement of the digestive organs). One preferred implant device of this invention has an elongated body equipped with at least one, and preferably two or more, electric poles that are electrically connected to an electric connection terminal for connection to a power source, a mechanism or device to penetrate the tissue or viscera to be treated, quick-release connecting devices to separate the penetration device from the elongated body, and a locking or attachment device which is capable of folding back and attaching to the elongated body whereby the locking or attachment device and the elongated body form a secure and essentially continuous loop around the tissue or viscera to be treated.

The improved implant device of the present invention is simple to handle and use, thereby simplifying the surgical procedure required to implant the device. This implant device can be easily inserted and anchored in the viscera to be stimulated without required suturing of the implant device to, or near, the tissue to be treated or requiring any maneuvers that might be difficult and risky for other viscera or for the integrity of the electrocatheter itself. This improved implant device with its attachment mechanism is especially adapted for electrostimulation and/or electrical monitoring of the tissue or viscera of the mammalian body (especially the human body), especially tissue and internal organs of the endo-abdominal cavity. Examples of such tissue and internal organs include, but are not limited to, the stomach, small intestine, large intestine, urinary bladder, gall bladder, muscles of the abdominal cavity, and tissue, muscles, and/or organs of the thoracic cavity (including, but not limited to, the cervical, thoracic and abdominal portions of the esophagus and the pharyngeal musculature in the neck), and the like. The present implant device can effectively lock onto and resist displacement from tissue or organs which undergo repeated and/or vigorous movement. Thus, the implant device of this invention are especially adapted and suitable for implantation in cases where the implant device is expected to remain for prolonged or extended periods of time.

It is one object of the present invention to provide a medical device to be used in laparoscopic surgery. Another object is to provide a medical device which allows easy insertion into the abdomen and/or removal from the abdomen through a trocar. It is another object of the invention to provide a medical device which can easily be attached to and locked on to the tissue or viscera of interest.

Still another object is to provide an implant device for attachment to internal tissue using laparoscopic surgery, said device comprising (1) an elongated body having a proximal end and a distal end and an essentially circular cross-section suitable for passage through a trocar used in laparoscopic surgery; and (2) an attachment mechanism at, or near, the distal end of the elongated body whereby the attachment mechanism can be folded back and attached to the elongated body so that the implant device is held in place and forms an essentially continuous loop around or through the tissue. Still another object of the invention is to provide an implant device specifically for electrostimulation and/or electrical monitoring of the endo-abdominal visceral tract that has significant flexibility of use since it is capable of having multiple poles and of being adapted to any surgical requirement without substantially modifying its structure.

Still another object is to provide an implant device for electrostimulation or electrical monitoring of tissue to be treated within the endo-abdominal cavity, said implant device comprising:

(1) an elongated body having a distal end and a proximal end, (2) a penetration mechanism at the distal end of the elongated body to penetrate the tissue to be treated, (3) a quick release connecting mechanism adjacent to the penetration mechanism which allows the penetration mechanism to be detached from the elongated body once the implant device has been properly located within the endo-abdominal cavity, (4) an attachment mechanism adjacent and proximal to the quick release connecting mechanism, wherein the attachment mechanism, once the penetration mechanism has been detached, can be folded back and attached to the elongated body so that the implant device is held in place and forms an essentially continuous loop around or through the tissue to be treated, (5) at least one electric pole located along the elongated body such that the electric pole is in electrical contact with the tissue to be treated when the attachment mechanism is folded back and attached to the elongated body, and (6) an electrical connection terminal at the proximal end of the elongated body for connection to a power source, wherein the electrical connection terminal is electrically connected to the electric poles. Preferably, the elongated body has two or more electric poles.

A further object of the invention is to provide an implant device specifically for electrostimulation or electrical monitoring of tissue to be treated within the endo-abdominal cavity, said implant device comprising: (1) an elongated body having a distal end and a proximal end, (2) a penetration mechanism at the distal end to penetrate the tissue to be treated, (3) a quick release connecting mechanism adjacent to the penetration mechanism such that the penetration mechanism can be removed from the elongated body once the implant device is properly positioned relative to the tissue to be treated, (4) an attachment mechanism adjacent to the quick release connecting mechanism, such that, when the quick release connecting mechanism is activated to remove the penetration mechanism, the attachment mechanism is at or near the distal end of the elongated body and the attachment mechanism can be folded back and attached to the elongated body to form an essentially continuous loop around or through the tissue to be treated and thereby secure the implant device to the tissue to be treated, (5) at least two electric poles located along the elongated body or the attachment mechanism so that, when the attachment mechanism is folded back and attached to the elongated body, the two or more electric poles can provide electrostimulation or electrical monitoring to the tissue within the loop, and (6) an electrical connection terminal at the proximal end for connection to a power source wherein the two or more electric poles are electrically connected to electrical connection terminal.

Still another object of the invention is to provide an implant device which, once anchored in the tissue or viscera to be treated, is capable of reducing to a minimum its excessive length inside the abdomen. Another object of the invention is to provide an implant device that effectively protects the electrical connection terminals that connects to a power source so as to be able to perform the implantation in a dry arena, thereby permitting the entire procedure, including anesthesia, to be carried out in an extremely short time.

These and other features and advantages of the present invention will become apparent to those skilled in the art upon a reading of the following detailed description, including the drawings.

BRIEF DESCRIPTION OF THE DRAWINGS

FIG. 1 is a schematic side view of one embodiment of the implant device according to this invention. This figure illustrate the implant device as initially inserted and located adjacent to the tissue to be treated, but prior to implementing the attachment mechanism.

FIG. 2 illustrate implant device of FIG. 1 where the penetration device has been removed via the quick release device, thereby exposing the attachment mechanism.

FIG. 3 illustrate the attachment mechanism of FIGS. 1 and 2 wherein the attachment mechanism has been implemented by folding it back over the elongated body and locking it in place around the tissue to be treated.

FIG. 4 a schematic side view of another embodiment of the implant device according to this invention.

FIG. 5 illustrates another embodiment of the attachment mechanism.

FIG. 6 illustrates another embodiment of the attachment mechanism.

FIG. 6A is a side view of the attachment mechanism wherein the attachment mechanism is locked in place with a suture.

FIG. 6B is a cross-sectional view of the attachment mechanism and the elongated body at position 26 wherein the attachment mechanism is locked in place with a surgical clamp.

FIG. 7 illustrates another embodiment of the attachment mechanism which ends in two prongs—one on either side of the elongated body.

FIG. 8 illustrates the attachment mechanism of FIG. 7 wherein the two prongs have been tied together using a suture so that the attachment mechanism surrounds the elongated body at position 26.

FIG. 9 illustrates another embodiment of the attachment mechanism wherein the elongated body has grooves adapted to receive the distal end of the attachment mechanism. The grooves allow the distal end of the attachment mechanism to be engaged at several positions along the elongated body. In FIG. 9, the distal end of the attachment mechanism has been positioned at the middle groove.

FIG. 10 illustrates still another embodiment of the attachment mechanism.

FIG. 10A provides a side view of the attachment mechanism wherein several flattened portions allow the attachment mechanism to more easily be folded back on the elongated body.

FIG. 10B is a cross-sectional view of the attachment mechanism at one of the flattened sections with reinforcing mechanism therein.

DETAILED DESCRIPTION OF THE PREFERRED EMBODIMENTS

The present invention provides an implant device specifically for electrostimulation and/or electrical monitoring of the endo-abdominal visceral tract. The implant device has an elongated body equipped with an integral attachment mechanism to secure it to the tissue to be stimulated and at least one electric pole, and preferably two or more electric poles, that are electrically connected to an electrical connection terminal for connection to a power source. The attachment mechanism folds or loops back and attaches to the elongated body, thereby forming an essentially continuous loop around or through the tissue to be treated. Using such an attachment mechanism, the implant device can be easily attached and anchored to the tissue to be treated. Preferably, the electric leads or poles are located on that portion of the elongated body which forms, with the attachment mechanism, the loop around the tissue to be treated.

Preferably the implant device also includes mechanism to penetrate the intestinal wall and a quick release connecting mechanism to separate the penetration device from the elongated body. Generally, the attachment mechanism is located proximal to the quick release mechanism so that, once the penetration device is separated from the elongated body, the attachment mechanism effectively is located at the distal end of the elongated body.

One embodiment of the present invention is illustrated in FIGS. 1–3. The implant device specifically for electrostimulation and/or electrical monitoring of the endo-abdominal viscera includes an elongated body, indicated by dimension line 50, with a distal end 52 and a proximal end 54. Located along the elongated body 50, and moving from the distal end 52 to the proximal end 54, are the penetration device or mechanism 8, the connection and quick-release mechanism 17, the attachment mechanism 20, the electrodes 24 and 25, the attachment position or element 26, and the electrical connection terminal pin 39 that is capable of connecting the implant device to a power source (not shown). The curved penetration device 8, which is capable of penetrating the intestinal wall and/or tissue, includes a solid tunneling device or stylet 14 with a smooth, noncutting curved section 12 having cutting part 10 on its distal end. Located opposite cutting part 10 is cavity 16 through which the attachment to the distal end of elongated body 50 is made through end 18 which is adapted to snugly fit into cavity 16. The connection and quick-release mechanism 17 includes a connecting element 18, one end of which is connected to the end of elongated body 50, and the other end of which is connected to the inside of cavity 16 on stylet 8. Located between the connection and quick release mechanism 17 and the two or more electrodes 24 is attachment mechanism 20. In this embodiment, attachment mechanism 20 contains a longitudinal slit 22 in and through the elongated body. The two or more electric poles 24 and 25 are electrically connected to an electrical connection terminal 33 that is capable of connecting the electrocatheter to a power source (not shown). The power source may be, for example, an electric pulsator with an operating frequency of a preset number of pulses per minute.

FIG. 2 illustrates the embodiment shown in FIG. 1 wherein the penetration mechanism or stylet 8 has been removed from the elongated body 50. Once the penetration device 8 has been removed, the attachment mechanism 20 forms the distal end of the elongated body 50. The attachment mechanism 20 can now be folded back to attach at attachment position 26 as shown in FIG. 3. The distal end of the attachment mechanism 20 can be attached or fixed to the elongated body at position 26 by any suitable mechanism. Once the attachment mechanism 20 is attached to the elongated body at position 26, an essentially continuous loop 100 is formed. The tissue to be treated (or at least a portion of such tissue) is normally within the loop 100 and in contact with electrodes 24, 25. FIG. 3 illustrates the implant device shown in FIGS. 1 and 2 wherein the loop 100 has been formed surrounding tissue 102. Of course, adjacent tissue 104 (e.g., stomach tissue) not within the loop 100 is also stimulated and/or monitored (and, thus, treated) since it is in contact with, or in close proximity to, electrodes 24 and 25.

The length of the connecting element 18 and attachment mechanism 20 are adjusted to permit angling and flexing without harming the electrical component located within the elongated body. Moreover, the length of attachment mechanism 20 is adjusted so that it can fold back along elongated body 50 and be attached to the elongated body 50 at position 26 and, in doing so, form a continuous loop around or through and around a portion of the tissue to be treated. The connecting element 17 and the distal end of the attachment mechanism 20 can be, and preferably are, radiopaque. As shown in FIG. 2, during video-laparoscopic surgery, in order to separate the stylet 8 from the elongated body 50 of the electrocatheter, it is sufficient to cut it with laparoscopic or endoscopic scissors 66 or other cutting devices in order to be able to remove the stylet or penetration mechanism 8 from the abdominal cavity. The electric poles 24 and 25 are electrically connected to an electrical connection terminal 33 that is capable of connecting the electrocatheter to a power source (not shown). The power source may be, for example, an electric pulsator with an operating frequency of a preset number of pulses per minute. Tissue 102 and tissue 104 (which is not within the loop 100 but which is in contact with electrodes 24 and 25) can now be stimulated or monitored as desired. Although two electrical poles 24 and 25 are shown in the drawings, a single electrical pole or more than two electrical poles can be used. Generally, however, two electrical poles are preferred.

The implant device may also include a cover or cap 34 that consists, for instance, of a removable and insulating sheath which has, in addition, sealing or binding element 27 which fits in groove 35 (see FIG. 2). The sheath includes a small covering, preferably of silicone or other biocompatible material, which prevents contamination and guarantees both the impermeability of connecting terminal 33 for the entire time it is in the abdomen during insertion, and during its recovery for electrical connection. The sealing element 27 on sheath 34 allows a watertight seal, prevents contact between the biological fluids and electric terminal 33, and prevents the sheath from breaking off by force of the traction to which it is subjected when the electrical connecting terminal is extracted from the abdomen. The sheath can be, moreover, equipped with a mechanism to recover the electrocatheter after implanting, which consists of ring 36 which can be attached to a thread or fine cord 37 of a predetermined length. The unattached end of thread 37 can remain outside the abdominal cavity and thereby permits recovery of the electric terminal end of the electrocatheter.

If desired, the elongated body may also have a series of graphic representations 30, each one of which is different from the other, which can be used to indicate the orientation and location of the electrocatheter during the implant procedure. The graphic representations 30 indicate to the surgeon the location of the two ends of the electrocatheter during the insertion operation. For example, the graphic representations could consist of black zebra stripes that increase in size as they move toward electric terminal 33. Of course, other graphic representations could be used so long as they allow the orientation and location of the electrocatheter to be determined visually (through the video camera) during the implantation procedure.

In addition, the elongated body 50 shown in FIGS. 1–3 may have a sliding cylindrical member 28 equipped with a seat 29 which permits it to be stopped at a desired position on the elongated body. This sliding cylindrical member 28 can be used, if desired, to more securely attach that attachment mechanism 20 to the elongated body at position 26. For example, once the continuous loop has been formed by attaching the distal end of attachment mechanism 20 to the elongated body 50, the sliding cylindrical member 28 can be positioned over position 26 to cover the attachment area, thereby protecting it and more securely locking it in place.

Thus, the implant device generally includes penetration mechanism 8, which is capable of penetrating the intestinal wall or other tissue, mechanism 17 for connection and quick-release of penetration mechanism 8 from the elongated body 50 of the electrocatheter, and attachment mechanism 20 which can be folded back over elongated body 50 for attachment to the elongated body 50 at position 26. The outer insulating cover on elongated body 50, connecting element 18, attachment mechanism 20, and other non-electrically conduction members which may come into contact with biological fluids are preferably formed from silicone (preferably medical grade) or other biocompatible material having similar stress characteristics.

The distance between the distal end of the attachment mechanism 20 and the attachment position 26 may be vary as needed, and will depend upon the desired distance between the electric poles 24 and 25 as well as the extent of the tissue to be treated or monitored. Thus, the distance between the distal end of the attachment mechanism and the attachment position 26 can be varied so that a continuous loop 100 can be formed around or through the tissue to be treated. As shown in FIG. 3, the continuous loop 100 is formed from the attachment position 26 through the elongated body containing the electric poles 24, through the attachment mechanism 20, and back to the attachment position 26.

The attachment mechanisms and implant devices using such attachment mechanisms are especially useful in laparoscopic surgery. In operation, once the patient has been given a general anesthesia and the appropriate trocars have been inserted, it is possible to maneuver from outside all the instruments that are used by means of a monitor that transmits the images from the video camera. At this point, the surgeon should see that sheath 34 is tightly secured by binding 35 to electrical terminal 38. Then the surgeon proceeds to connect thread 37 to ring 36 attached to sheath 34. After the electrocatheter is placed in the abdominal cavity, the surgeon may keep thread 37, which is anchored to said ring and must be of sufficient length, outside the abdomen. By means of the live images from the camera it is easy to identify the back end of the electrocatheter thanks to the zebra stripes 30 on it, and thus, stylet 8 which is secured by a needle holder or clamp is introduced into the thickness of the small gastric curve, taking care not to enter the gastric cavity. For this purpose, a gastroscopy may be performed during the tunneling operation.

Once penetration mechanism or stylet 8 has completed its journey (i.e., attachment mechanism 20 has passed through, for example, the transmuscular tunnel created by the penetration mechanism 8 and electrodes 24 and 25 are in proper position to stimulate or monitor the appropriate tissue), the penetration mechanism is removed from the implant device via the quick release device 17. Removal of the penetration mechanism exposes attachment mechanism 20 at the new distal end of the elongated body. The distal end of the attachment mechanism 20 is then folded back along the elongated body 50 and attached to the elongated body 50 at position 26 to form a continuous loop 100. The electrocatheter is effectively "locked" in place by the continuous loop 100 which effectively surrounds tissue 102. Positioned within the loop 100 and within the transmuscular tunnel are at least one electrical pole (and preferably two or more electrical poles) to stimulate tissue to be treated (e.g., nerves and muscles of the gastric wall).

Once the electrocatheter is properly positioned, the stylet 8 is then again secured with forceps, and quick release connecting element 17 is cut with endoscopic scissors 66 as shown in FIG. 2 along either dotted line A or B in FIG. 1 or dotted line B in FIG. 4. The stylet is then removed from the abdominal cavity of the patient. Once the attachment mechanism 20 is attached to the elongated body 50 at position 26, the electric terminal 33 may be extracted from the abdomen using thread 37 attached to ring 36 on sheath 34. Once the electric terminal is outside the abdomen, sheath 34 can be removed from electric terminal 33 in order to expose the electric terminal. The operation is thus performed in a dry arena. Electric terminal 33 is then connected to a pacemaker or a recorder, and the proper functioning of the system and the integrity of the electrocatheter are checked using appropriate instrumentation. If desired, the electrocatheter can be further anchored by means of conventional nylon or other suture to the abdominal wall (preferably to the muscular fascia). In this manner, the electrocatheter is secured in two positions: (1) around or through the tissue to be stimulated by continuous loop 100 and (2) to the abdominal wall via a suture.

As shown in FIGS. 2 and 3, once the penetration mechanism 8 is detached, attachment mechanism 20 is folded back on the elongated body 50. Depending on where cut is made to remove the penetration mechanism 8, the distal end 52 can be an single or double member. If the cut is made on dotted line A (i.e., so that the cut does not intercept slot 22), the distal end will have a solid end. FIG. 2 illustrates where the cut is made on dotted line A. If the cut is made on dotted line B (i.e., so that the cut intercepts slot 22), the distal end will have two ends. Attachment of the distal end 52 to attachment position 26 will, of course, depend on where the cut is made. If the cut is made at position A, the proximal end 54 of the elongated body 50 can be inserted into, and pulled through, slit 22. The elongated body is then worked through the slit 22 until the distal end (formed by cut A) is adjacent to position 26 and forms the continuous loop 100 (FIGS. 3 and 5). FIG. 5 more clearly illustrates the slit 22 through which the elongated body 50 passes. If desired, the distal end of the attachment member 20 and the elongated body at position 26 can be more securely attached using, for example, clamps, sutures, surgical string, other flexible thread materials, and the like.

If the cut is made at position B (see FIGS. 1 and 4), the two distal end of the attachment mechanism 20 are folded back over the elongated body 50 such that the distal ends or prongs are placed on opposite sides of elongated body 50 at position 26. The two ends or prongs may be bound together (with the elongated body 50 between them) using, for example, clamps, sutures, and the like, thereby forming a continuous loop 100 around or through the tissue to be treated. FIGS. 7 and 8 illustrate such attachment methods.

A simplified embodiment of an electrocatheter using the attachment mechanism 20 is shown in FIG. 4. In this embodiment, the stylet 8 is attached to the distal end of elongated body 50. The stylet 8 in this embodiment is attached to the elongated body 50 using a flexible tube 19 (preferably medical-grade silicone similar to the insulating cover of the elongated body 50) that fits over the end 18 of elongated body 50 and the hub 15 of stylet 8. The connection may be strengthened, if desired, using medical-grade adhesive and/or a thin wire joining the stylet 8 and the elongated body 50. Of course, if such a wire is used to strengthen the connection, it should be non-conducting or electrically isolated from the electrical circuit used for stimulation. The elongated body 50 has attachment mechanism 20 and attachment position 26 with the appropriate poles 24 and 25 located there between. The elongated body 50 terminates in electrical terminal 33 having electrical poles 38 and 39 at proximal end 54. In operation, the electrocatheter is placed and positioned in the same manner as described above for the embodiment shown in FIGS. 1–3. The electrical terminal 33, however, preferably remains outside the body cavity. Thus, once the electrocatheter has been correctly positioned within the body cavity and the attachment mechanism 20 attached to the elongated body 50 at position 26, the electrical terminal 33 can be attached to the appropriate power source. Thus, the simplified electrocatheter shown in FIG. 4 does not require the movable sheath 28 or cover 34 to protect the electrical terminal 33 since the electrical terminal 33 preferably remains outside the body cavity during the implantation procedure. Preferably the stylet 8 has one or more flattened portions 56 to help the surgeon grasp, manipulate, and guide the implant device to the proper position using forceps or other surgical instruments. Since electric terminal 33 is preferably kept outside the body cavity, the cut to remove the connection and quick-release mechanism 17 is preferably made at position B, thereby forming two distal ends or prongs 20A and 20B (FIG. 7). The continuous loop 100 can be made as described above and as illustrated in FIGS. 7 and 8.

In operation, the electrocatheter shown in FIG. 4 is placed using essentially the same surgical procedure as described above. Once in place, the two poles 38 and 39 of electrical terminal 33 are attached to a power source. One pole 38 of the electrical terminal 33 is electrically connected to one pole 24 and the other pole 39 of the electrical terminal 33 is electrically connected to the other pole 25 through the elongated body. The electrical circuit is completed via the tissue to be stimulated and/or monitored. Thus, as those skilled in the art will understand, the overall electrical circuit within the implant device runs from one pole 38 of the electrical terminal 33 along a first electrical path through the elongated body 50 to electric pole 24, through the tissue to be stimulated to the other electric pole 25, and then from the other electric pole 25 through a second and separate electric path through the elongated body 50 to the other pole 39 in the electrical terminal 33. As those skilled in the art will also realize, the materials of construction and the methods of making the electrical circuit for the implant devices of this invention, including the poles 24, 25, 38, and 39, as well as the internal electrical connections, are well known in the art.

As those skilled in the art will realize, numerous attachment mechanisms 20 can be used in the practice of this invention. For example, FIG. 6A illustrates the use of suture 110 to attach the distal end of attachment mechanism 20 to the elongated body at position 26 to form continuous loop 100. Suture 110 can be simply tied around the exterior surface of attachment mechanism 20 and elongated body 50 at position 26 or suture 110 could pass through one or both of the members to be attached. Notches, groves, or indentations for seating the suture 110 could be provided in one or both of the attachment mechanism 20 (towards its distal end) and the elongated body at position 26 to more securely form the continuous loop. Such notches, grooves, or indentations could, for example, be used to prevent the two members (i.e., attachment mechanism 20 and elongated body 50) from sliding relative to each other during vigorous action of the tissue or muscle to be stimulated; such an arrangement would also reduce the risk of the continuous loop being improperly tightening around and strangling the tissue to be treated. If desired, the distal end of attachment mechanism 20 could be flattened so that when it is attached to the elongated body 50 at position 26, it forms a less bulky attachment. A cross-sectional view (at position 26 of elongated body 50) of such a flattened attachment mechanism 20 is provided in FIG. 6B. The attachment of attachment member 20 to the elongated body 50 in FIG. 6B is effected using clamp 112 to secure the attachment rather than the suture 110 of FIG. 6A.

Other forms of such notches, grooves, or indentations could also be used. For example, the elongated member at position 26 could have notches, grooves, or indentations to receive one or more distal ends of attachment mechanism 20; once the one or more distal ends are located in the notch, groove, or indentation and secured by suture, clamps, or the like, movement of the attachment mechanism along the elongated body would be prevented. Indeed, the elongated body 50 could have a series of such notches, groves, or indentation at or around position 26 for receiving the distal end or ends of attachment device 20. By selecting different locations on the elongated body at which to attach or anchor attachment device 20, the surgeon could vary the circumference of continuous loop 100 depending on the extent of tissue is to be surrounded and treated. Such a series of notches 80 are illustrated in FIG. 9. Preferably the notches 80 are angled at about 45 to 60 degrees (relative to the long axis of the elongated body 50) so as to better receive the distal end(s) of attachment mechanism 20; of course, other angles or confirmations of the notches 80 could be used. Such notches 80 can be used with, for example, the attachment mechanism 20 illustrated in FIGS. 5, 7, and 8 (i.e., wherein the penetration mechanism is removed by cutting at either dotted line A or B in FIG. 1). As discussed above, the movable sheath 28 could also be adapted to more securely attach the attachment mechanism 20 to the elongated body 50. Such a movable sheath 28 could be adapted to slide over position 26 and the distal end of the attachment mechanism 20 and then be locked in place (using, for example, suture 31 which fits in indentation 29 in FIG. 2).

FIGS. 7 and 8 illustrate a further method of forming the desired continuous loop 100 and thereby locking the implant device to the tissue to be treated. In FIG. 7, the distal end of the attachment mechanism 20 forms two prongs 20A and 20B (such prongs could be formed by cutting along dotted line B in FIGS. 1 or 4). The two prongs 20A and 20B of attachment mechanism 20 are placed on either side of the elongated body at position 26 (or other appropriate position along the elongated body). The prongs 20A and 20B are preferably located within notches or grooves 80 (see FIG. 9) on the elongated body 50 so as to prevent excessive tightening or constriction of the tissue 102 to be treated. Then, as shown in FIG. 8, the two prongs 20A and 20B are tied, sutured, or clamped together. If desired, additional sutures 110 or clamps (not shown) could be used to more firmly attach the attachment member to the elongated member (i.e., as shown in FIGS. 6A and 6B).

The attachment mechanism 20 can have one or more flattened or thinned regions 82 (FIG. 10A) to allow the attachment mechanism 20 to more easily be folded back on the elongated body. A cross-sectional view of a flattened region 82 is provided in FIG. 10B. The attachment mechanism 20 can also have internal reinforcing mechanisms 84 (e.g., wire, suture, or the like). Such reinforcing mechanisms or devices are well known in the art. If the reinforcing mechanisms are electrical conductors, care should be taken to isolate the reinforcing mechanisms from the electrical circuit including poles 24, 25, 38, and 39. Reinforcing mechanisms (84 in FIG. 10B) are especially preferred in the flattened or thinned regions 82. Similar internal reinforcing mechanisms can also be used as appropriate to strengthen the elongated body 50.

As those skilled in the art will realize, a wide variety of mechanisms, as well as combinations of those mechanisms, can be used to secure or lock the distal end of attachment mechanism 20 to the elongated body 50. Such mechanisms include, for example, sutures as illustrated in FIGS. 6A and 8, clamps as illustrated in FIG. 6B, notches 80 to receive the attachment mechanism as illustrated in FIG. 9, intersecting mechanism (i.e., elongated body 50 passing through slot 22 in the attachment mechanism) as illustrated in FIG. 5, and similar clamping or locking devices known in the surgical arts. Generally, it is preferred that attachment mechanism 20 is firmly and securely attached to the elongated body 50 at position 26 so as to prevent the continuous loop 100 from tightening around the tissue 102 and possibly damaging such tissue. Such a more secured attachment is especially preferred when the implant device is used with, or attached to, stomach muscle or tissue.

As noted above, the attachment mechanism should securely hold the implant in place during the time period at which stimulation or monitoring is carried out. Preferably, the implant should also be easily removable when desired (e.g., after treatment or monitoring is complete or for any other reason). The implant device can be removed using essentially the same procedures as used for its implantation (i.e., laparoscopic surgery using appropriate trocars and surgical instruments). For example, the attachment mechanism 20 can be cut in one or more locations along continuous loop 100 and then removed, along with the remainder of the implant device. To minimize trauma to the tissue (especially the tissue surrounding and forming the penetration tunnel), it is preferred that the attachment mechanism be cut as close as possible to the exit portion of the tunnel in order to minimize the portion of the attachment mechanism which is pulled through the tunnel during removal. The sutures or clamps used to lock the distal end of the attachment mechanism to the elongated body can be removed if desired; removal of such sutures or clamps may allow for smaller diameter trocars be used when removing the implant device.

Also as those skilled in the art will realize, that attachment mechanism 20 could be adapted to be used in a wide variety of surgical implant devices. For example, the attachment mechanism 20 could be adapted to the implant devices or electrocatheters described in our PCT Application PCT/US98/10402, filed May 21, 1998, and our copending U.S. patent application Ser. No. 09/122,832, filed on Jul. 27, 1998, which are both hereby incorporated by reference. The attachment mechanism 20 is especially adapted for use with surgical implant devices adapted for laparoscopic techniques and surgery and similar procedures. Moreover, the attachment mechanism and implant devices modified with such attachment mechanism are specially adapted for attachment to organs and muscle tissue which are subject to strong and/or periodic movements. Thus, for example, the present invention is especially adapted for stimulation and/or monitoring of tissue or muscle of the stomach; such tissue is subjected to the rippling, peristaltic movement associated with digestion. Thus, the present invention is even more adapted to provide electrical stimulation to the stomach for treating obesity and/or syndromes related to motor disorders of the stomach as described in U.S. Pat. No. 5,423,872 (issued Jun. 13, 1995), which is hereby incorporated by reference. In such a method, the implant device could be surgically attached, using attachment mechanism 20, at the level of the distal gastric antrum of the patient by laparoscopic techniques. Such an implant device or stimulator would normally have an operating frequency of greater than about 2 pulses per minute (preferably about 2 to 25 pulses per minute and more preferably about 2 to 16 pulses per minute) in order to eliminate or reduce the motility of the stomach, so as to slow down or prevent gastric transit therein and/or improve the functionality of the lower esophageal and pyloric sphincter for a preset time.

It has been proven in practice that the attachment mechanism, either alone or in conjunction with the implant devices and/or handles described herein, according to the invention is particularly useful as stated above. The invention so described may be subject to numerous modifications and variations, all of which fall within the scope of the inventive concept; furthermore, all the details may be replaced by technically equivalent elements. In practice, the materials used, as well as the dimensions, may be varied according to need and the state of the art. Although this attachment mechanism alone or in combination with the implant device has been mainly described relative to its use in the gastrointestinal organ/tract, it can be used in the endo-abdominal cavity to simulate or monitor viscera therein; such viscera include, but are limited to, tissues associated with pharynx and esophagus from the neck through chest to the abdomen, the stomach, small and large intestines, gall bladder, urinary tract, urinary bladder, muscles, and the like. Moreover, although this implant device has been described in the context of use within the endo-abdominal cavity, it can, of course, be used in other portions of the body with appropriate modifications.

What is claimed is:

1. An implant device for attachment to internal tissue using laparoscopic surgery, said implant device comprising:
   (1) an elongated having a proximal end and a distal end and an essentially circular cross-section suitable for passage through a trocar used in laparoscopic surgey;
   (2) an attachment mechanism at, or near, the distal end of the elongated body whereby the attached mechanism can be folded back and attached to the elongated body so that the implant device is held in place and forms an essentially continuous loop around or through the tissue; and
   (3) two or more electric poles located along the elongated body such that the electric poles are in electrical contact with the tissue when the attachment mechanism is folded back and attached to the elongated body,
   wherein the electric poles are connected to an electrical connection terminal for connection to a power source and
   wherein the attachment is an elongated slot in the elongated body at or near the distal end of the elongated body, whereby the attachment mechanism can be folded back and the proximal end of the elongated body can extend through the slot to form the essentially continuous loop and to secure the attachment mechanism to the elongated body.

2. The implant device as defined in claim 1, wherein the elongated body includes one or more grooves adapted for accepting and positioning the attachment mechanism at one or more predetermined locations along the elongated body.

3. The implant device as defined in claim 1, further comprising a slidable member on the elongated body adapted for assisting in locking the attachment mechanism to the elongated body.

4. The implant device as defined in claim 1, wherein the attachment mechanism includes one or more thinned regions to allow the attachment mechanism to more easily be folded back over the elongated body.

5. The implant device as defined in claim 4, wherein the attachment mechanism is an elongated slit at or near the distal end of the elongated body such that two extending prongs can be formed, whereby the attachment mechanism can be folded back such that the two prongs of the attachment mechanism can be placed on opposite sides of the elongated body and secured to the elongated body.

6. The implant device as defined in claim 5, wherein the elongated body includes one or more grooves adapted for accepting and positioning the attachment mechanism at one or more predetermined locations along the elongated body.

7. The implant device as defined in claim 5, further comprising a slidable member on the elongated body adapted for assisting in locking the attachment mechanism to the elongated body.

8. The implant device as defined in claim 5, wherein the attachment mechanism includes one or more thinned regions to allow the attachment mechanism to more easily be folded back over the elongated body.

9. An implant device for electrostimulation or electrical monitoring of tissue to be treated within the endo-abdominal cavity, said implant device comprising:
   (1) an elongated body having a distal end and a proximal end,
   (2) a penetration mechanism at the distal end of the elongated body to penetrate the tissue to be treated,
   (3) a quick release connecting mechanism adjacent to the penetration mechanism which allows the penetration mechanism to be detached from the elongated body once the implant device has been properly located within the endo-abdominal cavity,
   (4) an attachment mechanism adjacent and proximal to the quick release connecting mechanism, wherein the attachment mechanism, once the penetration device has been detached, can be folded back and attached to the elongated body so that the implant device is held in place and forms an essentially continuous loop around or through the tissue to be treated,
   (5) one or more electric poles located along the elongated body such that the electric poles are in electrical contact with the tissue to be treated when the attachment mechanism is folded back and attached to the elongated body, and
   (6) an electrical connection terminal at the proximal end of the elongated body for connection to a power source, wherein the electrical connection terminal is electrically connected to the electric poles.

10. The implant device as defined in claim 9, wherein two or more electric poles are located along the elongated body.

11. The implant device as defined in claim 10, wherein the attachment mechanism is an elongated slot in the elongated body at or near the distal end of the elongated body, whereby the attachment mechanism can be folded back and the proximal end of the elongated body can extend through the slot to form the essentially continuous loop and to secure the attachment mechanism to the elongated body.

12. The implant device as defined in claim 11, wherein the elongated body includes one or more grooves adapted for accepting and positioning the attachment mechanism at one or more predetermined locations along the elongated body.

13. The implant device as defined in claim 11, further comprising a slidable member on the elongated body adapted for assisting in locking the attachment mechanism to the elongated body.

14. The implant device as defined in claim 11, wherein the attachment mechanism includes one or more thinned regions to allow the attachment mechanism to more easily be folded back over the elongated body.

15. The implant device as defined in claim 10, wherein the attachment mechanism is an elongated slit at or near the distal end of the elongated body such that two extending prongs can be formed, whereby the attachment mechanism can be folded back such that the two prongs of the attachment mechanism can be placed on opposite sides of the elongated body and secured to the elongated body.

16. The implant device as defined in claim 15, wherein the elongated body includes one or more grooves adapted for accepting and positioning the attachment mechanism at one or more predetermined locations along the elongated body.

17. The implant device as defined in claim 15, further comprising a slidable member on the elongated body adapted for assisting in locking the attachment mechanism to the elongated body.

18. The implant device as defined in claim 15, wherein the attachment mechanism includes one or more thinned regions to allow the attachment mechanism to more easily be folded back over the elongated body.

19. An implant device specifically for electrostimulation or electrical monitoring of tissue to be treated within the endo-abdominal cavity, said implant device comprising:
   (1) an elongated body having a distal end and a proximal end,
   (2) a penetration mechanism at the distal end to penetrate the tissue to be treated,
   (3) a quick release connecting mechanism adjacent to the penetration mechanism such that the penetration mechanism can be removed from the elongated body once the implant device is properly positioned relative to the tissue to be treated,
   (4) an attachment mechanism adjacent to the quick release connecting mechanism, such that, when the quick release connecting mechanism is activated to remove the penetration mechanism, the attachment mechanism is at or near the distal end of the elongated body and the attachment mechanism can be folded back and attached to the elongated body to form an essentially continuous loop around or through the tissue to be treated and thereby secure the implant device to the tissue to be treated,
   (5) at least two electric poles located along the elongated body or the attachment mechanism so that, when the attachment mechanism is folded back and attached to the elongated body, the two or more electric poles can provide electrostimulation or electrical monitoring to the tissue within the loop, and
   (6) an electrical connection terminal at the proximal end for connection to a power source wherein the two or more electric poles are electrically connected to electrical connection terminal.

20. The implant device as defined in claim 19, wherein two electric poles are located along the elongated body or the attachment mechanism.

21. The implant device as defined in claim 19, wherein the attachment mechanism is an elongated slot in the elongated body at or near the distal end of the elongated body, whereby the attachment mechanism can be folded back and the proximal end of the elongated body can extend through the slot to form the essentially continuous loop and to secure the attachment mechanism to the elongated body.

22. The implant device as defined in claim 21, wherein the elongated body includes one or more grooves adapted for accepting and positioning the attachment mechanism at one or more predetermined locations along the elongated body.

23. The implant device as defined in claim 21, further comprising a slidable member on the elongated body adapted for assisting in locking the attachment mechanism to the elongated body.

24. The implant device as defined in claim 21, wherein the attachment mechanism includes one or more thinned regions to allow the attachment mechanism to more easily be folded back over the elongated body.

25. The implant device as defined in claim 19, wherein the attachment mechanism is an elongated slit at or near the distal end of the elongated body such that two extending prongs can be formed, whereby the attachment mechanism can be folded back such that the two prongs of the attachment mechanism can be placed on opposite sides of the elongated body and secured to the elongated body.

26. The implant device as defined in claim 25, wherein the elongated body includes one or more grooves adapted for accepting and positioning the attachment mechanism at one or more predetermined locations along the elongated body.

27. The implant device as defined in claim 25, further comprising a slidable member on the elongated body adapted for assisting in locking the attachment mechanism to the elongated body.

28. The implant device as defined in claim 25, wherein the attachment mechanism includes one or more thinned regions to allow the attachment mechanism to more easily be folded back over the elongated body.

* * * * *

UNITED STATES PATENT AND TRADEMARK OFFICE
CERTIFICATE OF CORRECTION

PATENT NO. : 6,510,332 B1
DATED : January 21, 2003
INVENTOR(S) : Robert J. Greenstein It is certified that error appears in the above-identified patent and that said Letters Patent is hereby corrected as shown below:

Column 14,
Line 29, after "elongated" insert -- body --.
Line 46, after "attachment" insert -- mechanism --.
Lines 46 and 50, change "slot" to -- slit --.

Columns 14-15, Lines 65-67 and 1-4,
Replace Claim 5 with the following:

```
      5. An implant device for attachment to internal tissue using
laparoscopic surgery, said implant device comprising:
      (1) an elongated body having a proximal end and a distal end and an
essentially circular cross-section suitable for passage through a trocar
used in laparoscopic surgery;
      (2) an attachment mechanism at, or near, the distal end of the
elongated body whereby the attachment mechanism can be folded back and
attached to the elongated body so that the implant device is held in
place and forms an essentially continuous loop around or through the
tissue; and
      (3) two or more electric poles located along the elongated body
such that the electric poles are in electrical contact with the tissue
when the attachment mechanism is folded back and attached to the
elongated body,
      wherein the electric poles are connected to an electrical
connection terminal for connection to a power source; and
      wherein the attachment mechanism is an elongated slit at or near
the distal end of the elongated body such that two extending prongs can
be formed, whereby the attachment mechanism can be folded back such that
the two prongs of the attachment mechanism can be placed on opposite
sides of the elongated body and secured to the elongated body.
```

Column 15,
Lines 48 and 52, change "slot" to -- slit --.

UNITED STATES PATENT AND TRADEMARK OFFICE
CERTIFICATE OF CORRECTION

PATENT NO. : 6,510,332 B1
DATED : January 21, 2003
INVENTOR(S) : Robert J. Greenstein It is certified that error appears in the above-identified patent and that said Letters Patent is hereby corrected as shown below:

Column 16,
Lines 54 and 58, change "slot" to -- slit --.

Signed and Sealed this

Fifth Day of August, 2003

JAMES E. ROGAN
*Director of the United States Patent and Trademark Office*